US007155273B2

(12) United States Patent
Taylor

(10) Patent No.: US 7,155,273 B2
(45) Date of Patent: Dec. 26, 2006

(54) BLANCHING RESPONSE PRESSURE SORE DETECTOR APPARATUS AND METHOD

(76) Inventor: Geoffrey L. Taylor, 211 Oak Street, Winnipeg, Manitoba (CA) R3M 3P7

( * ) Notice: Subject to any disclaimer, the term of this patent is extended or adjusted under 35 U.S.C. 154(b) by 848 days.

(21) Appl. No.: 10/208,450

(22) Filed: Jul. 29, 2002

(65) Prior Publication Data

US 2004/0054303 A1 Mar. 18, 2004

(51) Int. Cl.
*A61B 8/14* (2006.01)
*G01N 33/48* (2006.01)
*G01D 18/00* (2006.01)

(52) U.S. Cl. ........................ 600/476; 600/473; 702/19; 702/104

(58) Field of Classification Search ................ 600/476, 600/407, 323, 326, 340, 504, 477, 473, 475; 200/500, 3.7, 52; 356/436, 432, 433; 702/19, 702/104

See application file for complete search history.

(56) References Cited

U.S. PATENT DOCUMENTS

| | | | | |
|---|---|---|---|---|
| 4,797,000 | A * | 1/1989 | Curtis | 356/436 |
| 5,588,437 | A * | 12/1996 | Byrne et al. | 600/504 |
| 6,222,411 | B1 * | 4/2001 | Chu et al. | 327/295 |
| 6,411,907 | B1 * | 6/2002 | Lu et al. | 702/28 |
| 6,631,288 | B1 * | 10/2003 | Bain et al. | 600/476 |
| 6,785,568 | B1 * | 8/2004 | Chance | 600/340 |
| 6,862,542 | B1 * | 3/2005 | Lockhart et al. | 702/76 |
| 2003/0144584 | A1 * | 7/2003 | Mendelson | 600/323 |

* cited by examiner

*Primary Examiner*—Brian L. Casler
*Assistant Examiner*—Jennifer A Horwat
(74) *Attorney, Agent, or Firm*—William L. Chapin

(57) ABSTRACT

A portable, hand-holdable Blanching Response Tester apparatus (BRT) pressable against the skin of a human patient to provide an indication of a non-blanchable erythema indicative of an incipient pressure sore includes a housing having in a front end wall thereof an optically transmissive window and within the housing a broad-band light source electrically energizable to emit light including energy in the near infrared (0.8μ to 1.5μ) outwards through the window. A first, leading photodetector spaced laterally apart from the light source and a second, trailing photodetector spaced equidistant from the light source in an opposite direction have fields of view which include regions of the skin ahead of an behind a central area of the skin illuminated by the light source. Electronic signal processing circuitry within the BRT housing includes a pair of differential amplifiers having opposite pairs of inputs connected to the pair of photodetectors, one amplifier driving a first, "NO-GO" red, light-emitting diode mounted in an upper wall panel of the housing, and the other amplifier driving a second, "GO" green LED. When the BRT window is pressed against the skin and the light source energized, if light reflected from the skin by leading photodetector over a questionable area of the skin exceeds light reflected from a known healthy sample area of skin beneath the trailing photodetector the red, NO-GO LED is illuminated if the difference in light values exceeds a first threshold values signifying a pressure sore, and if light received by the trailing photodetector exceeds that received by the leading photodetector by a second threshold value, the green, GO LED is illuminated.

11 Claims, 14 Drawing Sheets

3, 30, 103, 89, 25, 20, 82, 83, 21, 27, 26, 22, 80, 23, 50, 51, 3, 24

20
21
25
27
26
30
80
23
51
24
3
3
103
89
82
83
22
50

103
25
29
23
28
24
51
30
20
21
27
26

25
44
20
27
24
33
35T
36
46
31
26

46
34T
32
36
44
33
34L
31

30
21
42T
37
42L
38
84
20
80

90
105,107
98
102
101
96L
97R
92
104,106
92
97L
99
100
91
93,94

48
POWER/ DISPLAY
P8
+5V
+1.5V
GND
BAT+
BAT−
RED
GRN
EXTERNAL CHARGING CONTACTS
52
50
51
BAT+
BAT−
59
P81
45
SIGNAL PROCESSOR
+5V
+1.5V
GND
SIGA
SIGB
RED
GRN
B+
B−
BAT+
BAT−
47
49
SENSORS
46
A
LAMP
B
35T
33
35L 48 (1 OF 3)

BAT+
+5V
L1
E
81
D3
SW1
D
82
60
3
VIN
8
SW
U5
C7
5
STARTUP
VOUT
12
2
VGD
1
C
C4
U5
MODULATION CONTROL CIRCUIT
JP1
B
RESB
5
RESET CONTROL CIRCUIT
CT
4
SD/FB
6
GND
5V REGULATOR
7
60
C5
BAT+
A

TO POWER SUPPLY/DISPLAY
71
VL3
RED
72
VT3
GREEN
+5V
C11
R2
R1
48
47
RP1.B
2
7
RP1.D
4
5
U3.B
69
U3.D
70
VL2
VT2
RP2.D
4
5
RP2.B
2
7
B+
B−
58
PS2
RP2.C
3
6
U3.A
67
RP2.A
1
8
U3.C
68
RP1.A
1
8
RP1.C
3
6
D1
52
65
VL1
SIGA
66
VT1
SIGB
50
BAT+
51
BAT−
FROM SENSOR BOARD 112
115a
115b
117
115c
R=80
G=46
B=30
R=80
G=44
B=30
R=80
G=42
B=30
116
113
R=80
G=48
B=34
R=80
G=48
B=34
R=80
G=48
B=34
115
114a
R=80
G=46
B=30
R=80
G=44
B=30
R=80
G=42
B=30
114b
116
114c

BLANCHING RESPONSE PRESSURE SORE DETECTOR APPARATUS AND METHOD

BACKGROUND OF THE INVENTION

A. Field of the Invention

The present invention relates to methods and apparatus for detecting incipient or first stage pressure sores in humans. More particularly, the invention relates to a hand-held detector apparatus which is pressed against the skin of a patient to provide detection of non-blanchable erythemas which are indicative of existing or potential pressure sores, and a method for detecting pressure sores.

2. Description of Background Art

If an external part of a person's body is subjected to a localized external pressure sufficient to inhibit blood flow to tissue below the skin for substantially long periods of time, a sore or lesion can develop at the area of the skin where the pressure is applied. Such sores are referred to as pressure sores, and are common among medical patients and elderly persons who are required to lie in a hospital bed or be seated in a wheel chair for extended time periods. Typically, pressure sores develop in areas of tissue which overlie a bony prominence of the body. Even a relatively light pressure exerted by covering bed clothes on the toes of a recumbent patient is sufficient to cause a pressure sore on the toe, if exerted for a long period of time. The probability of a pressure sore forming is proportional to both the magnitude of the pressure and the time period which the pressure is exerted. Accordingly, areas of the body on which large portions of a patient's weight are supported by a bed or wheel chair are particularly likely candidate areas for the formation of a pressure sore in a relatively short period of time. These include the heels, ischial tuberosities at the ends of the hip bones, sacrum, scapula, and occiput (back part of the skull).

While the exact mechanism for the formation of the beginning or first stage pressure sore is not known, it is known that a prolonged deficiency of oxygenated blood supplied to tissues is a primary cause of the pathology. Prolonged here means longer than a localized and temporary deficiency of blood supply to an area of tissue caused by obstruction of blood flow to that area, a condition known as ischemia, which can cause a temporary whitening or blanching of the skin.

Temporary or short term ischemias can be induced by pressing the thumb against an area such as the back of the hand for a short time with pressure sufficient to cause noticeable whitening or blanching of the skin in the area of the thumb print. In healthy tissue, the normally colored, non-blanched appearance of the skin is restored within a few seconds after removal of pressure. If sufficient pressure is exerted on a body part for extended periods of time, especially over a bony prominence, a pressure sore can develop into a bed sore, or decubitus ulcer, defined as an ischemic necrosis and ulceration of tissue, can occur. As stated above, such pressure can be applied as a result of prolonged confinement in a fixed position in a bed or wheel chair, or from a cast or splint.

Pressure or decubitus ulcers are a severe problem in aged or convalescing individuals because advanced stages of such ulcers can result in loss of tissue, muscle, and bone, in second, third and fourth stages of severity, sometimes necessitating an amputation and occasionally resulting in death of the patient. Put succinctly, pressure ulcers are easy to acquire, slow to heal and expensive to treat. For these reasons, it is desirable to detect pressure ulcers in their earliest, first stage, so that the cause of the sore, such as insufficiently frequent re-positioning of a patient, may be rectified, and the sore treated to prevent its developing into a more severe pathology.

One indication of an incipient, or first stage pressure sore is a non-blanchable erythema (reddening) of intact skin, which, if not detected and treated, would develop into a lesion or ulcer. Such non-blanchable erythemas are believed to develop in response to external localized pressures as small as a few mm Hg, sufficient to displace haemoglobins and other fluids from tissues.

When the skin is temporarily subjected to external pressures above a few mm Hg, haemoglobins and other tissue fluids are displaced to adjacent areas of lower pressure, via normal pathways (veins, arteries, and lymph system). Whitening of the skin in this condition is known as the blanch or blanching response. When pressure is released from healthy tissue, the skin returns to its normal color after a short period of time. If, however, pressure is applied to the body of a sufficient magnitude and duration, blood and other tissue fluids spread interstitially. In that case, the pooled up fluids can no longer be displaced by external test pressure, and signify damage to the tissue. This condition is defined as a non-blanched erythema, or first stage pressure sore. A first stage pressure sore as described appears as a defined area of persistent redness in lightly pigmented skin, wherein darker skin tones, the sore may appear with persistent red, blue or purple hues.

Haemoglobins and other skin fluids have specific spectral reflectance characteristics. As tissue is damaged, the reflection spectra change as more of the fluids remain trapped interstitially. This results in pressure—damaged tissues having a generally higher spectral reflectance in the visible and near infrared portions of the electromagnetic spectrum. However, in dark skinned individuals, the pigment melanin in the skin causes the skin to have a relatively high optical density or opacity, thus masking differential spectral responses between healthy and pressure-damaged tissues in individuals having heavily pigmented skin. Thus, while a nurse or other medical professional can relatively reliably perform blanching response tests for pressure sores in light-skinned individuals, such tests are much less reliable when used on dark-skinned individuals.

In response to the problem of performing blanching response tests on dark-skinned individuals, the present inventor inter alia performed a study in an effort to eliminate the problem. The results of that study were summarized in a paper titled "Eliminating the Issue of Pigmented Skin Assessment of Blanch Response," contained in "Advances in Skin And Wound Care," Volume 14 #4, July/August 2001, published by Springhouse Corp. 1111 Bethleham Pike, P.O. Box 908, Springhouse, Pa. 19477. That study indicated that highly pigmented individuals have a higher incidence of Stage II ulcers than lightly pigmented individuals, and that near infrared spectroscopy is useful in the in vivo analysis of blood in tissues. Over the near infrared wavelengths of 650–900 nm, oxy-and deoxyhemoglobin are the dominant absorbing species in skin. The molecular structure of these two forms are significantly different, causing them to have distinctly different absorption spectra. Also, absorption of melanin in the near infrared portion of the electromagnetic spectrum is substantially less than in visible light. This fact, coupled with the ability of near infrared spectroscopy to monitor the relative concentrations of oxy-and deoxyhemoglobin, suggested that a near infrared spectroscopic examination should permit a spectroscopic-based blanch that is less dependent of skin pigmentation than manual blanch response tests.

The study results indicated that the inclusion of a melanin spectrum in the analysis of in vivo absorption spectra permitted the determination of the relative amounts of oxy-and deoxyhemoglobin in darkly pigmented as well as light-skinned individuals. The study also found significant differences in the quantity of each of these species at high and low pressure. In general, the study results indicated that the possibility of developing a spectroscopic-based blanch test which would be applicable to both fair and dark-skinned individuals.

Bain et al., in International Publication No. WO 00/603491 published Oct. 12, 2000, discloses a skin evaluation apparatus comprising a probe head having an emitter and sensor and a blanching edge. The emitter consists of bundles of optical fibres by means of which light from LEDs is delivered to and recovered from the skin. In use, the probe head is held flush with the skin surface causing the blanching edge to indent a fixed area of skin causing a local blanche. As the probe head is moved, the blanching edge slides along the skin surface evacuating blood as it moves. During the blanche, the LEDs are switched on and the scattered signal collected using a photodiode. A processor measures the attenuation of scattered light and gives a display of blood content against time, providing an indication of the blood circulation in that area.

The present invention was conceived of in response to a perceived need for a low cost, simplified, non-dispersive, hand-held detector for use in detecting incipient or first stage pressure sores, without entailing the complexity and cost of spectral analysis elements and functions, and which provides a static indication of incipient pressure sores without requiring that a moving head contact sensitive areas of the skin.

OBJECTS OF THE INVENTION

An object of the present invention is to provide a pressure sore detector which provides an indication of a non-blanchable erythema in tissues below the skin of a human patient.

Another object of the invention is to provide pressure sore tester which utilizes a blanching response to distinguish between healthy skin and tissue, and pathologically damaged skin and tissue.

Another object of the invention is to provide a blanching response tester which utilizes differential reflection of light from two adjacent areas of skin to determine if a tested area exhibits a non-blanchable erythema indicative of a pressure sore.

Another object of the invention is to provide a blanching response detector which utilizes a light source spaced laterally apart from a photodetector, both of which have optical axes that are positionable obliquely or perpendicularly to the surface of the skin of a patient, the photodector receiving a percentage of the source light reflected from blood and other fluids below the skin in proportion to the quantity and spectral characteristics of the fluids.

Another object of the invention is to provide a blanching response tester which includes a light source spaced laterally apart from a pair of photodectors, the source and photodetectors all having optical axes which are positionable obliquely to the skin surface of a patient, one photodector receiving light emanating from the source and reflected from a first, healthy sample area of skin, and the other photodector receiving light emanating from the source and reflected from a test area of the skin, a larger amount of light above a predetermined threshold reflected from the test area indicating a non-blanchable erythema.

Another object of the invention is to provide a hand-held blanching response tester for non-blanchable erythemas which includes a window behind which is located a light source and a pair of photodetectors, the optical axes of the source and photodector being spaced laterally apart from one another and so arranged that pressing the window against the skin with a predetermined pressure sufficient to cause blanching in an area of healthy skin will cause a portion of light reflected from a healthy sample area of skin and tissue beneath one photodetector to be a predetermined percentage below light reflected from a test area of skin below the other photodetector which has a non-blanchable erythema.

Another object of the invention is to provide a blanching response tester for non-blanchable erythemas which includes a window behind which is located a light source for illuminating a body part pressed against the window, a first photodetector located on a first, leading side of the light source, a second photodetector located on a second, trailing side of the photodetector, a first amplifier and LED driver having an input connected to an output of the leading photodetector and an output connected to a first, red LED, a second amplifier and LED driver having an input connected to the output of the trailing photodetector and an output connected to a second, green LED, and associated control circuitry which causes said red LED to being illuminated, giving a positive indication of a non-blanchable erythema from reflected light received by the leading photodetector from a test area of the skin exceeding a predetermined threshold percentage of the source light, and causing the green LED to be illuminated when light reflected from a healthy sample area of skin to the trailing photodetector exceeds the light received by the leading photodetector, by a predetermined threshold percentage.

Another object of the invention is to provide a method for detecting non-blanchable erythemas symptomatic of incipient pressure ulcers comprising the steps of illuminating an external surface of area of skin of a human with a broadband visible light source while exerting pressure on the area, detecting a portion of the source light reflected from a test area of the human's body with a first photodetector, detecting a portion of the source light reflected from a healthy sample surface of the body with a second photodetector, comparing signals output from the first and second photodetectors, providing a positive indication of a non-blanchable erythema if the output signal from the first photodetector exceeds that from the second photodetector by a predetermined percentage, and providing a negative indication indicating a healthy, blanchable test area if the output signal from the second photodetector exceeds that from the first photodetector by a predetermined percentage.

Various other objects and advantages of the present invention, and its most novel features, will become apparent to those skilled in the art by perusing the accompanying specification, drawings and claims.

It is to be understood that although the invention disclosed herein is fully capable of achieving the objects and providing the advantages described, the characteristics of the invention described herein are merely illustrative of the preferred embodiments. Accordingly, we do not intend that the scope of our exclusive rights and privileges in the invention be limited to details of the embodiments described. We do intend that equivalents, adaptations and modifications of the invention reasonably inferable from the description contained herein be included within the scope of the invention as defined by the appended claims.

SUMMARY OF THE INVENTION

Briefly stated, the present invention comprehends a method and apparatus for detecting pressure sores in human beings, particularly in the early or incipient stages of development of such sores. The method and apparatus utilize a blanching response test to detect non-blanchable erythemas which are characteristic of first stage pressure sores. Use of the method and apparatus according to the present invention is particularly effective on dark skinned individuals having a relatively high content of melanin in the skin, highly pigmented skin generally prevents effective use of normal thumb-pressure blanching tests for non-blanchable erythemas, since dark skin does not usually blanch sufficiently to be readily visible to the eye.

A blanching response tester for non-blanchable erythemas according to the present invention includes a relatively broad band light source, e.g., an incandescent lamp such as a tungsten lamp, operated at a temperature which results in an approximately black body emission peaking in the visible portion of the spectrum, but having a significant portion of energy emitted by the near infrared region of the electromagnetic spectrum. For example, a tungsten lamp operated at about 2900° K, and producing a peak emission at about 0.5 μm, and significant energy emission in the near IR range of 0.8 to 1.5 μm is a suitable light source for the present invention.

A blanching response tester apparatus according to the present invention also includes at least one pair of photodetectors having optical axes generally parallel to and spaced laterally apart from the optical axis of the illumination pattern of the light source. The light source and photodetectors are located behind the rear surface of an optically transparent window, the front surface which is pressable against the outer surface of the skin of a human patient to produce a blanching response in the skin. In a preferred embodiment of the invention, a first, leading photodetector is located on a first, leading side of the illumination source, and a second, trailing photodetector is located on an opposite, trailing side of the illumination source.

The apparatus includes a first electronic amplifier having an input terminal connected to an output terminal of the leading photodetector, and a first output indicator, e.g., a red light emitting diode (LED), connected to an output amplifier. Similarly, the apparatus includes a second electronic amplifier which has an input terminal connected to an output terminal of the trailing photodetector, and an output terminal connected to the input terminal of a second output indicator, e.g., a green LED. When the window of the apparatus is pressed against a skin surface and the illumination source energized, a percentage of visible and IR energy incident upon the skin surface is reflected back into the entrance pupils or apertures of the leading and trailing photodetectors, a greater percentage into that photodetector overlying a non-blanchable erythema. If the difference in reflected light received by the two photodetectors exceeds a predetermined threshold value, the indicator coupled to that photodetector amplifier circuit is energized, while the other indicator remains un-energized.

A method for detecting pressure sores according to the present invention includes positioning a first light detector means, e.g., a leading photodetector, over an area of suspect skin, positioning the second light detector means, e.g., a trailing photodetector, over a healthy area of skin, applying a normal force which exerts pressure on an area of the skin including the healthy sample area and the suspect area, illuminating with a broad band light source an area of the skin including that lying under the two photodetectors, energizing a first, positive indicator means, e.g., a red LED if the light energy received by the photodetector overlying a suspect area exceeds a first predetermined threshold value, and energizing a second, negative indicator means, e.g., a green LED, if the light received from a healthy skin area exceeds a predetermined threshold value.

DESCRIPTION OF THE PREFERRED EMBODIMENTS

FIGS. 1–13 illustrate a Blanching Response Tester (BRT) detector apparatus for detecting pressure sores according to the present invention.

Figure 1:
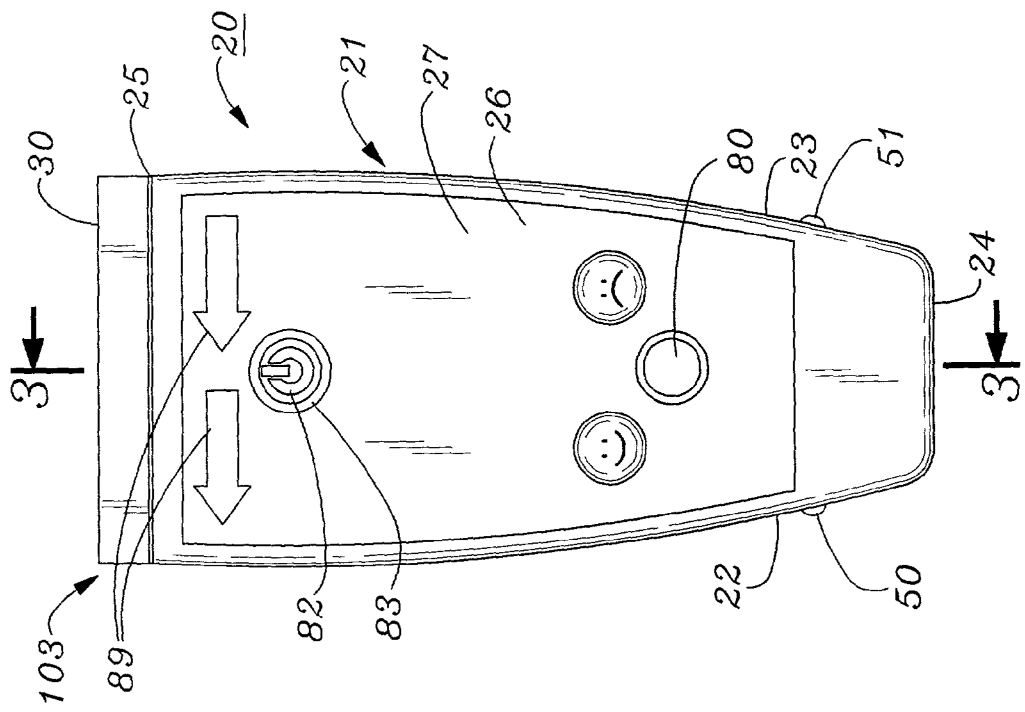
FIG. 1 is an upper plan view of a Blanching Response Tester (BRT) detector apparatus for detecting pressure sores according to the present invention.

Referring first to FIGS. 1–6, a blanching response tester (BRT) test apparatus 20 according to the present invention may be seen to include a housing or case 21 having in upper and lower plan views an approximately rectangular shape, which is longitudinally elongated and modified by left and right mirror symmetric side walls 22, 23 that curve arcuately inwardly rearward of a vertical transverse medial plane of the housing. Thus, as shown in FIG. 1, tester apparatus 20 has a laterally disposed rear vertical end wall 24 which is laterally centrally located with respect to the front end wall 25 of housing 21, but of smaller width than the front end wall.

Figure 2:
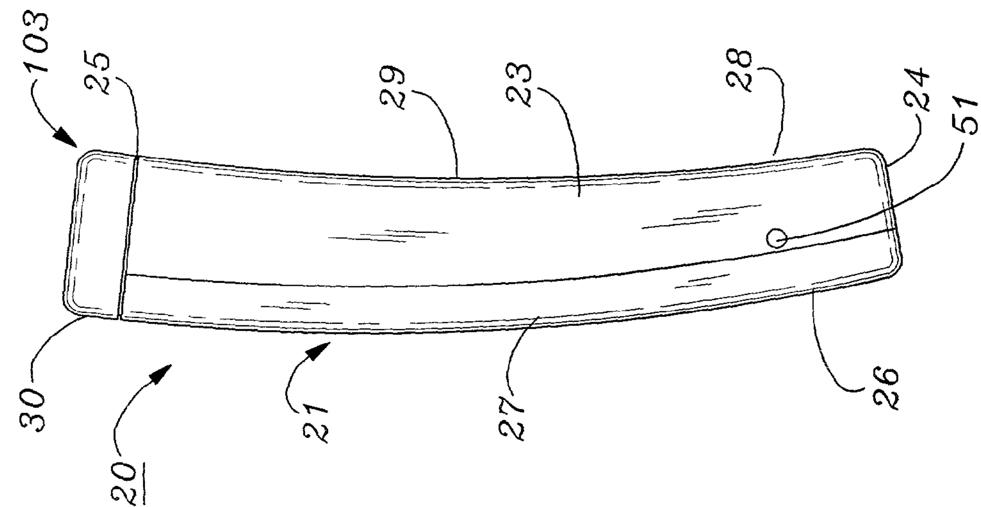
FIG. 2 is a right-side elevation view of the apparatus of FIG. 1, the left side elevation view being mirror symmetric therewith.
Figure 8:
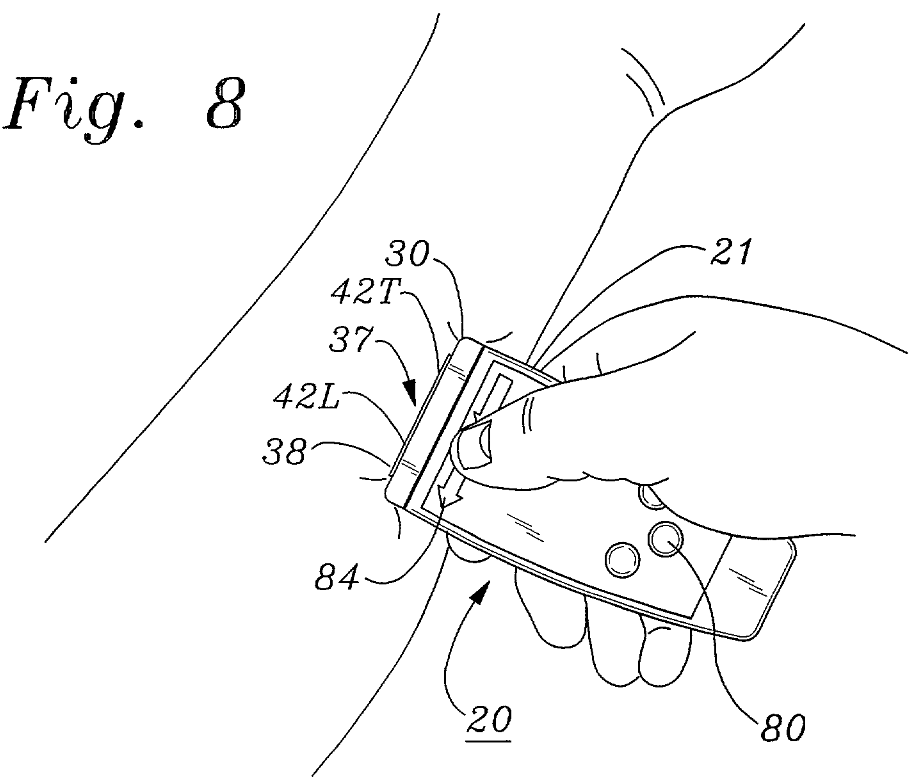
FIG. 8 is a perspective view showing the apparatus of FIG. 1 in use.

As may be seen best by referring to FIG. 2, housing 21 of BRT detector apparatus 20 has an upper wall 26 that has a slightly arcuately curved, convex upper surface 27, and a lower wall 28 having a slightly greater, arcuately curved concave lower surface 29. The exact shape of BRT detector apparatus housing 21 is not critical, but, as so far described, and shown in FIG. 8, is preferably of a shape and size which enables the device to be conveniently held in and operated by a human hand.

Figure 3:
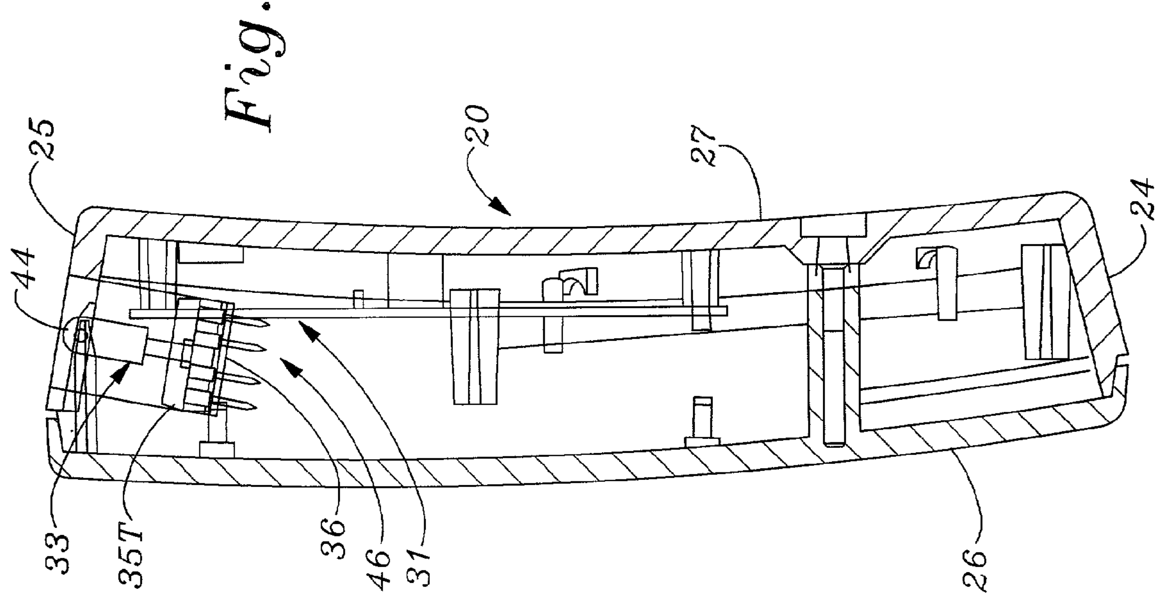
FIG. 3 is a fragmentary vertical medial longitudinal sectional view of the apparatus of FIG. 1, taken along line 3—3.
Figure 4:
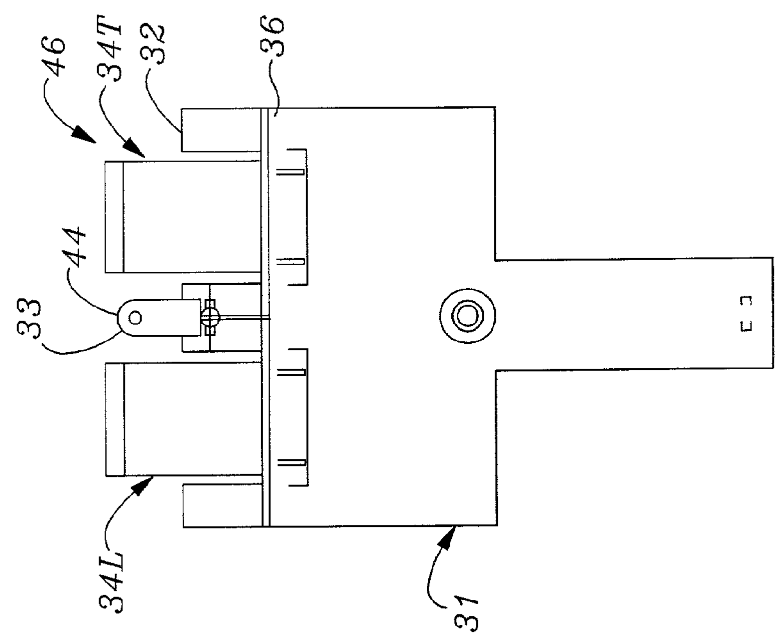
FIG. 4 is a fragmentary view of the structure of FIG. 3, showing a circuit board on which are mounted a light source and a pair of photodetector assemblies comprising parts of the apparatus.
Figure 5A:
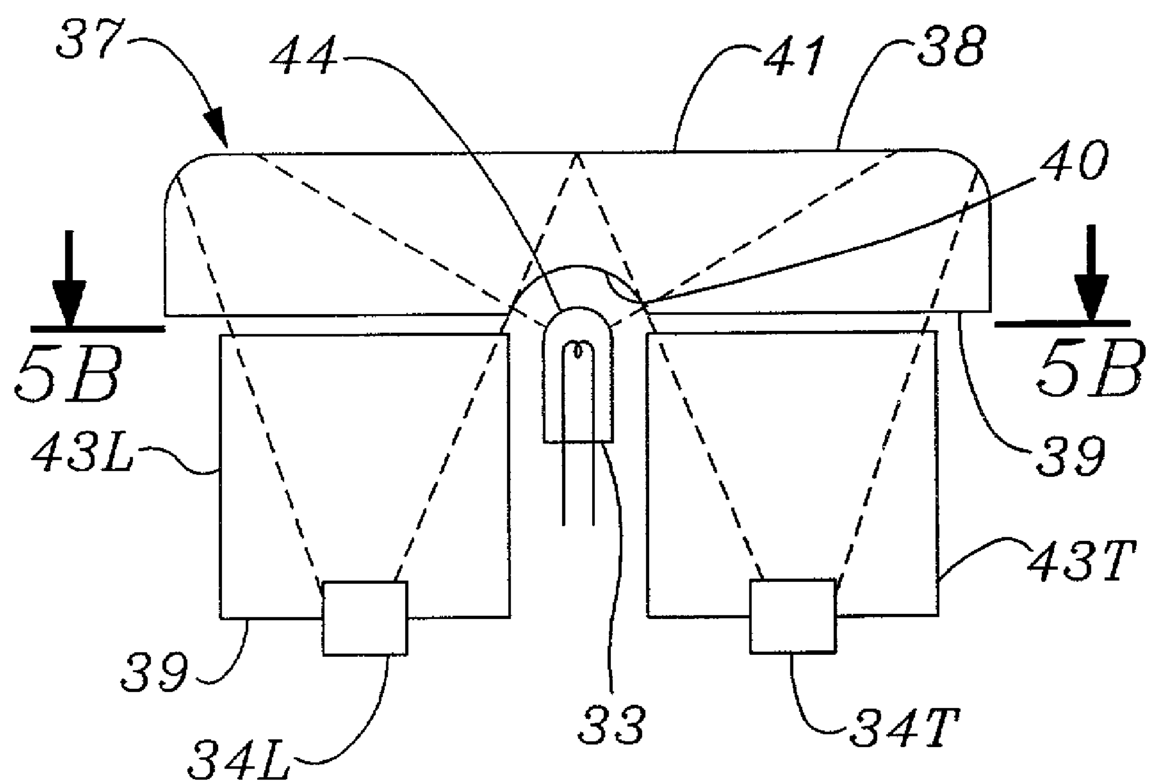
FIG. 5 is an upper plan view of a window comprising part of the apparatus of FIG. 1.
Figure 5C:
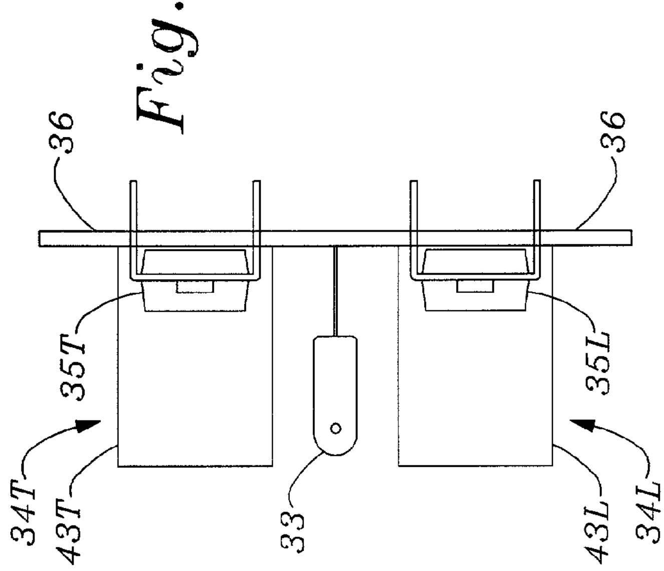
Figure 5B:
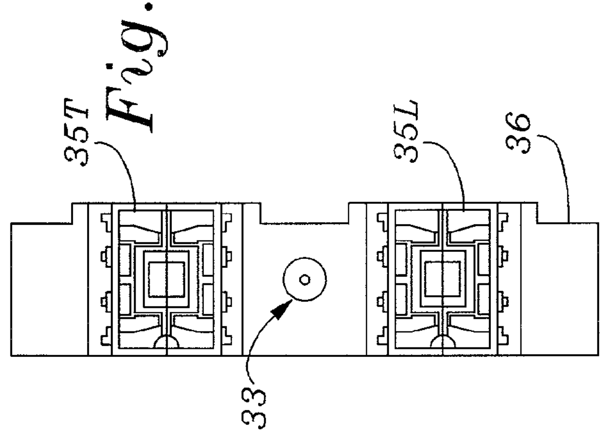
Figure 5D:
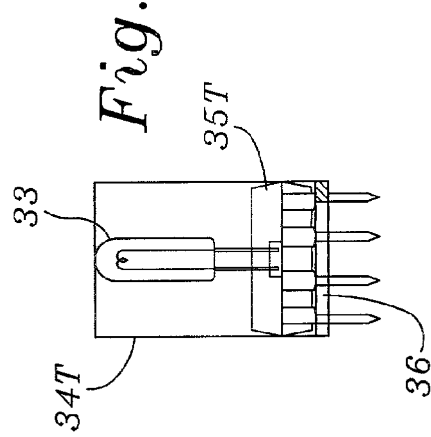
Figure 6:
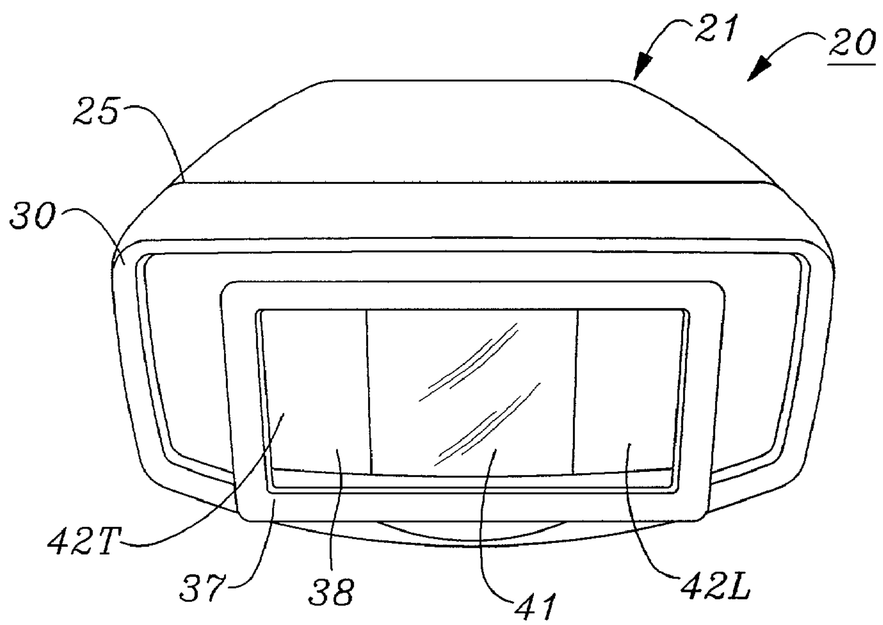
FIG. 6 is a front end elevation view of the apparatus of FIG. 1.
Figure 7:
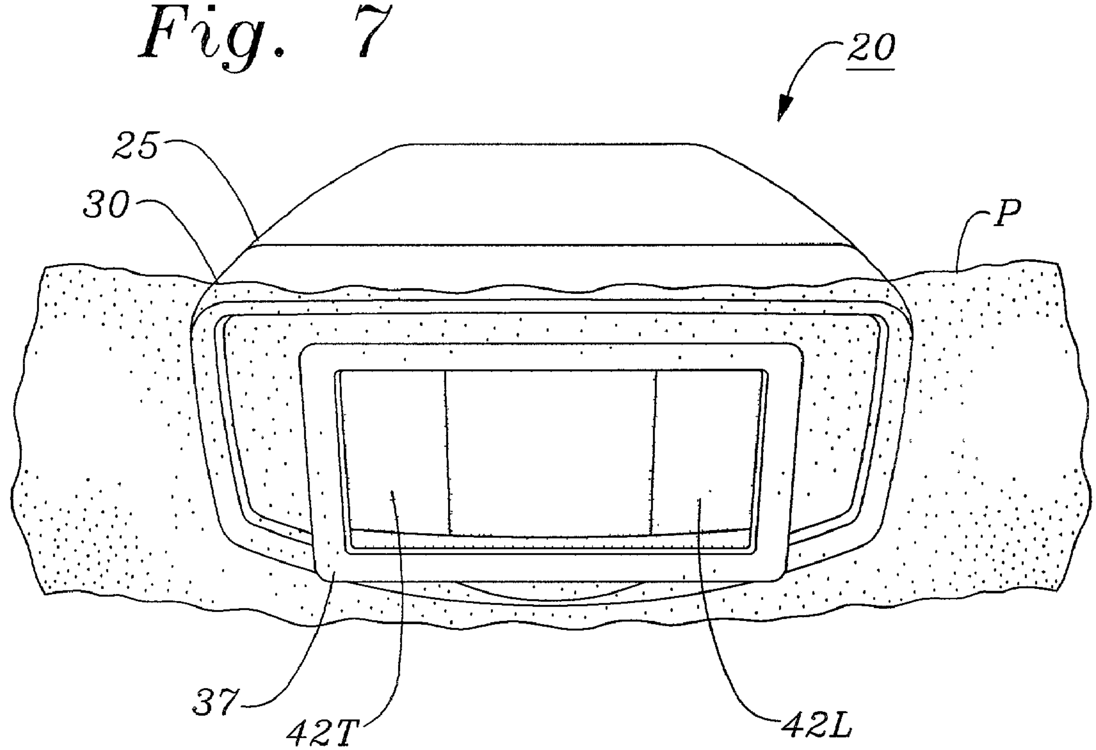
FIG. 7 is a front end elevation view of the apparatus similar to that of FIG. 6, but showing the light source of the apparatus turned on and a tissue paper adhered temporarily to a window of the tester to reveal the illumination pattern of the light source.

As shown in FIGS. 1, 2 and 6, housing 21 of BRT detector apparatus 20 has attached at front transverse vertical end wall 25 thereof a window cap 30 having in front end elevation view (FIG. 6) a generally laterally elongated rectangular shape approximating the transverse sectional shape of housing 21. As shown in FIGS. 3–6, BRT tester apparatus 20 includes within housing 21 a main electronic circuit board or mother board 31, on which is mounted near a first edge 32 thereof, a laterally centrally located illumination source 33. Also mounted on motherboard 31 are a pair of photodetector assemblies 34. As shown in FIGS. 3, 4, and 6, photodetector assemblies 34L, 34T are located on opposite, "leading" (left) and "trailing" (right) lateral sides of illumination source 33, and are equidistant therefrom.

As shown in FIGS. 3 and 4, each photodetector assembly 34L, 34R has a generally rectangular plan view integrated circuit photodetector 35 that includes a silicon photodiode and associated biasing and amplification circuitry. Each photodetector 35 is mounted on a photodectector circuit board 36 that has a laterally elongated, generally rectangular shape and which protrudes upwardly from motherboard 31. As shown in FIG. 3, photodetector circuit board 36 is angled forward slightly from motherboard 31, thus orienting the photodetector circuit board parallel to downwardly and rearwardly angled front transverse end wall 25 of housing 21.

As shown in FIGS. 2, 5, 6, window cap 30 of tester 20 fits conformally to front vertical end wall 25 of housing 21. Cap 30 has a laterally elongated rectangular shape, and holds concentrically therewithin a laterally elongated, optically transmissive window comprising a lens block 37. Lens block 37 has a generally flat front, or outer surface 38, and a generally flat rear or inner surface 39. The latter has protruding inwardly thereof a laterally centrally located, arch-shaped notch 40. As shown in FIG. 6, front surface 38 of lens block 37 has a laterally centrally located, laterally elongated and rectangularly-shaped area 41 which is made diffusely light transmissive by lightly sand blasting front surface 31. Lens block 37 also has a pair of generally square-shaped, left and right transparent portions 42L, 42R, respectively. The latter are aligned with and contacted at their respective rear surfaces with the front edges of a pair of square cross section, tubular light baffles 43L, 43R, which are in turn contacted at rear edge walls thereof with photodetectors 34L, 34R, respectively.

Figure 10:
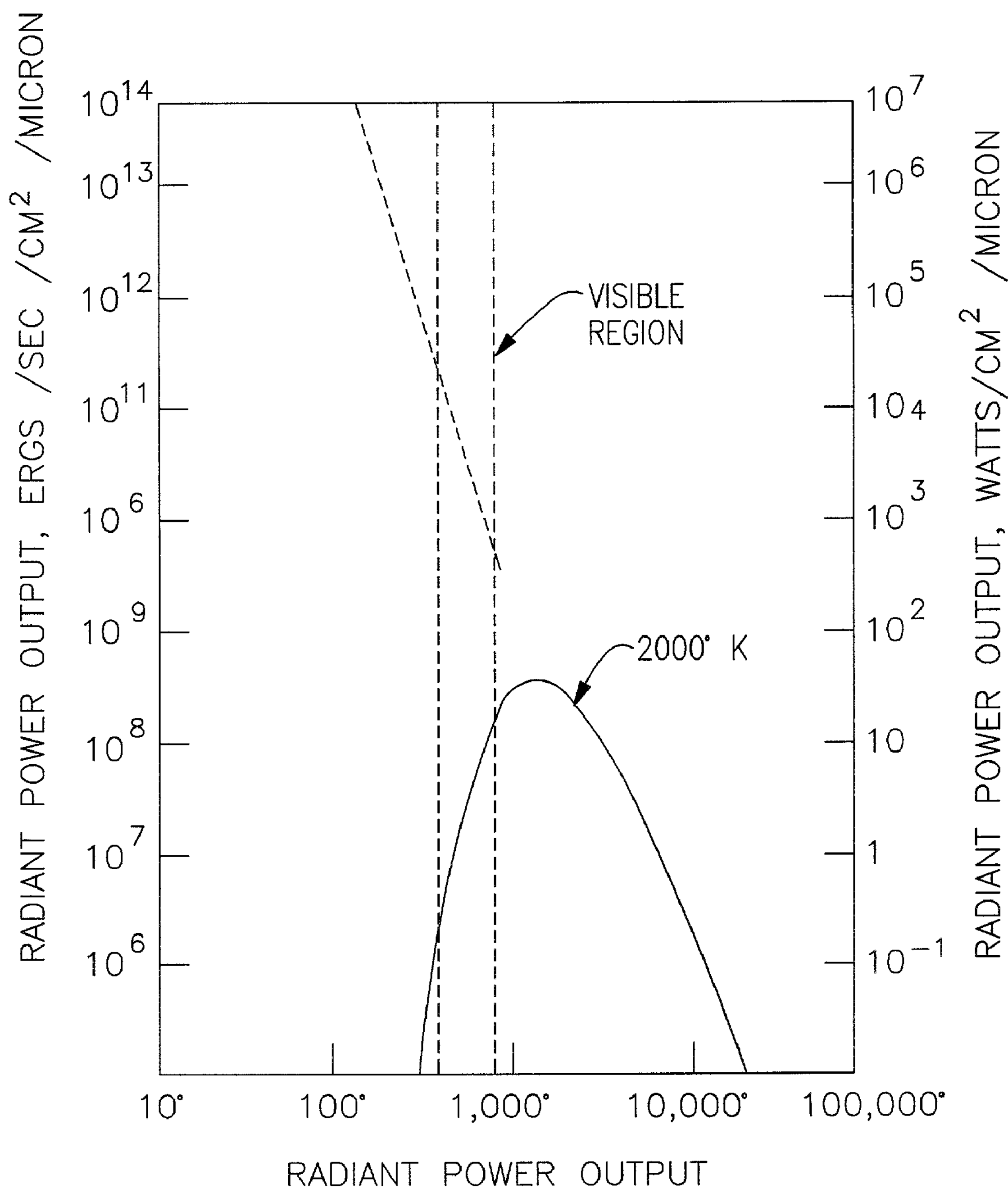
FIG. 10 is a graph showing a spectral emission or black-body radiation curve which indicates relative radiant power output verses wavelength of the light source of the apparatus of FIG. 1.

Referring now to FIGS. 3 and 4, it may be seen that illumination or light source 33 comprises a generally tubular shaped, electrically energized, tungsten filament lamp having a generally hemispherically-shaped front end window 44. In a sample embodiment of tester 20 tested by the inventor, light source 33 comprised a model 107-000-220 lamp obtained from Mag-lite, Inc., Ontario, Calif., operated at a color temperature of about 2900° K. As shown in FIG. 10, lamp 33 operated at about 2900° K radiates a relatively large percentage of its total energy output in the visible portion of the electromagnetic spectrum comprising the wavelength range of about 450 nanometers to 750 nm, and a smaller percentage of its energy in a near infrared portion of the spectrum comprising the wavelength range of about 750 nm to about 1,000 nm.

Figure 11:
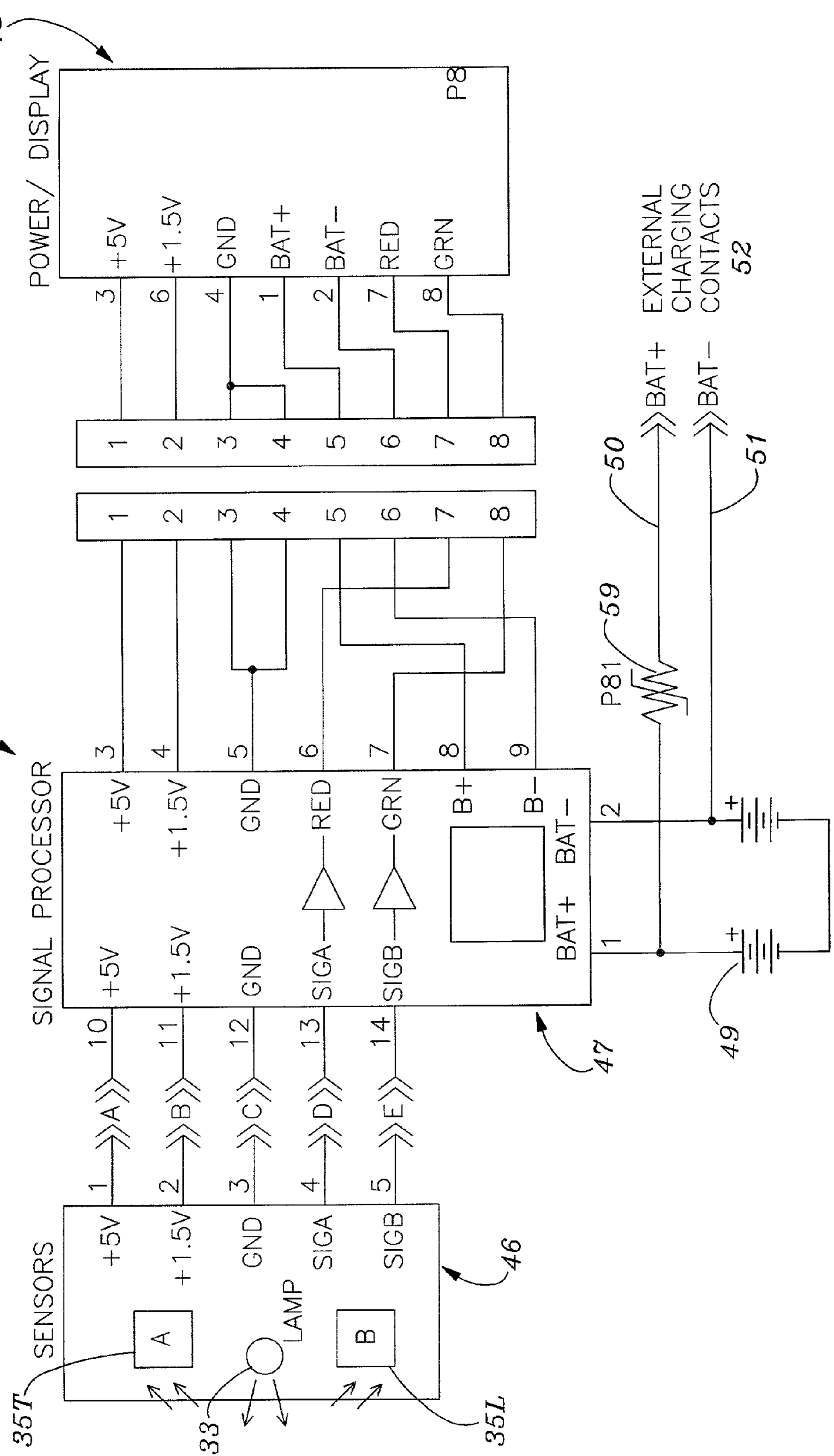
FIG. 11 is a block diagram of the apparatus of FIG. 1.

Blanching response tester 20 according to the present inventor includes electrical and electronic elements which are operably interconnected with photodetector 35L, 35R, and lamp 33, the structure and function of which may be best understood with reference to FIGS. 11 and 12.

Referring first to the block diagram of FIG. 11, it may be seen that BRT tester 20 includes electronic circuitry 45, which is mounted on motherboard 31 and electrically connected to photodetectors 35L, 35T. As shown in FIG. 11, electronic circuitry 45 comprises three electrically and operatively interconnected functional modules or blocks including an optical head module 46, a signal processing module 47, and a power conditioner/display module 48. As shown in FIG. 11, circuitry 45 of tester 20 is powered by a rechargeable battery 49 contained within tester housing 21. Battery 49 is connectable by a pair of positive and negative terminals 50, 51 to an external charging voltage source 52. As shown in FIGS. 11 and 12, circuitry 45 includes power conditioning circuitry consisting of a reverse polarity protection diode 52 connected across charging input terminals 50 and 51, and a pair of current limiting thermistors 58, 59 connected in series with the positive battery terminal and charger, and the positive battery terminal and other portions of circuitry 45, respectively.

Figure 12A:
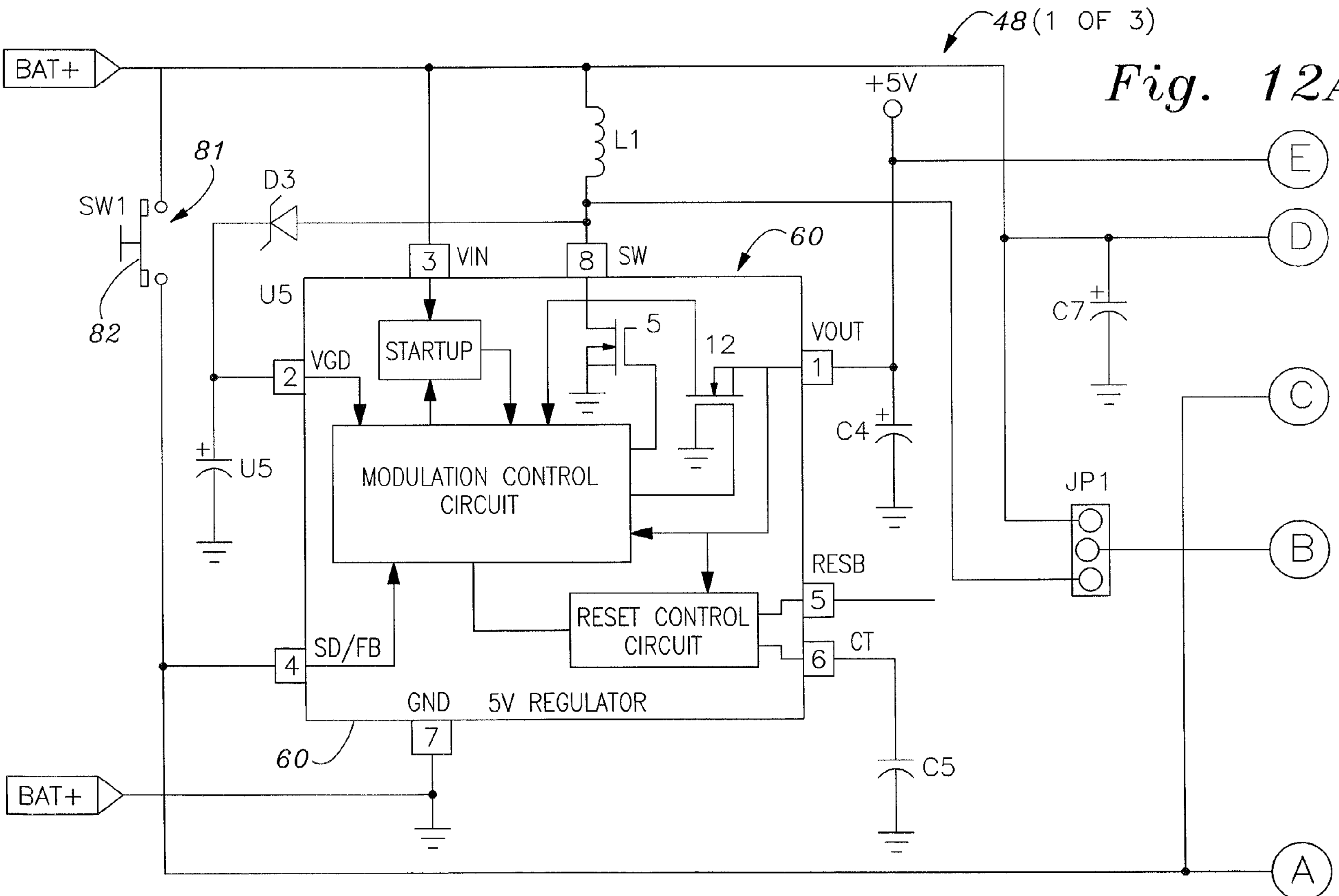
FIG. 12 is a schematic diagram of the apparatus of FIG. 1.
Figure 12B:
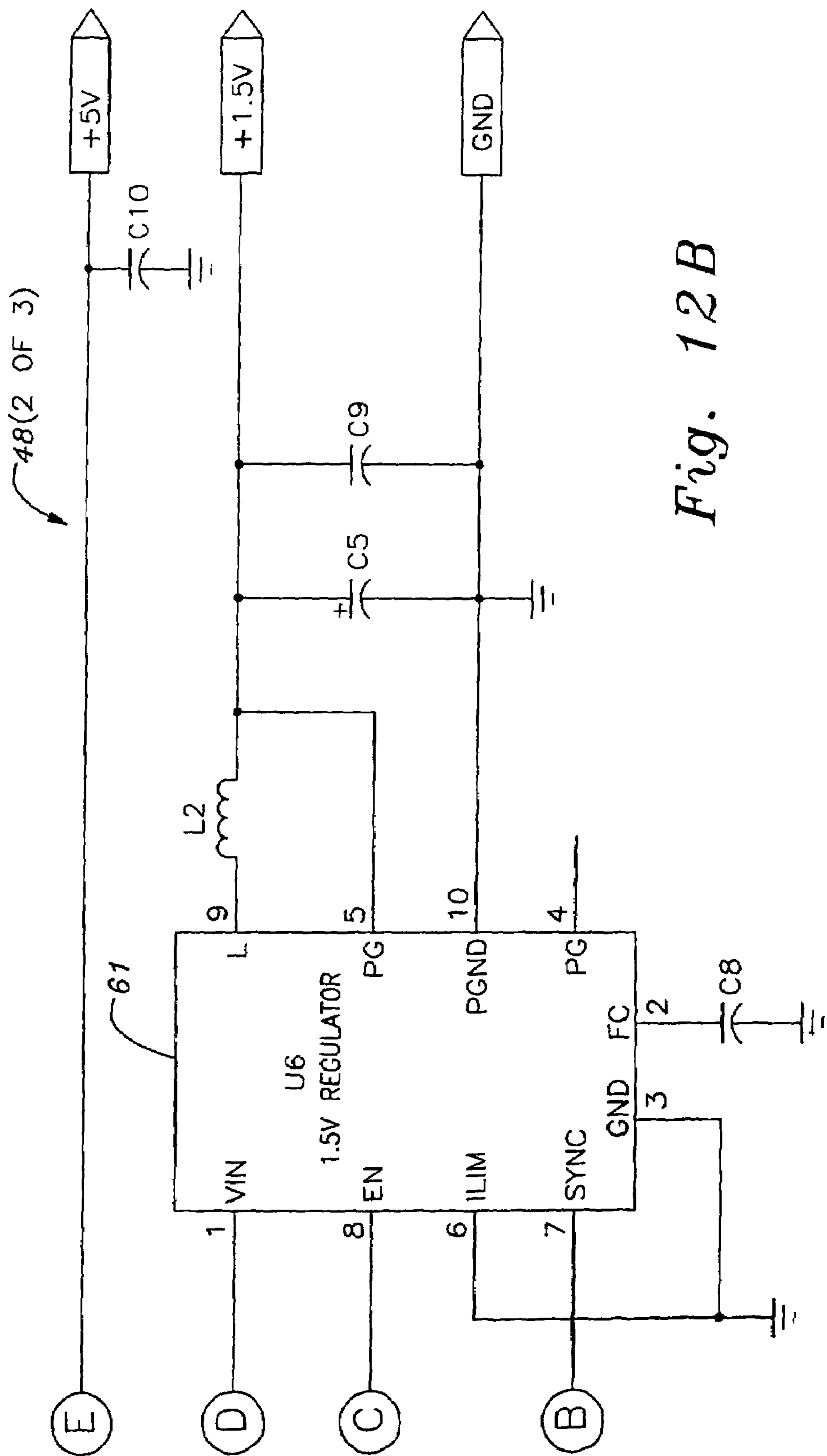
Figure 12C:
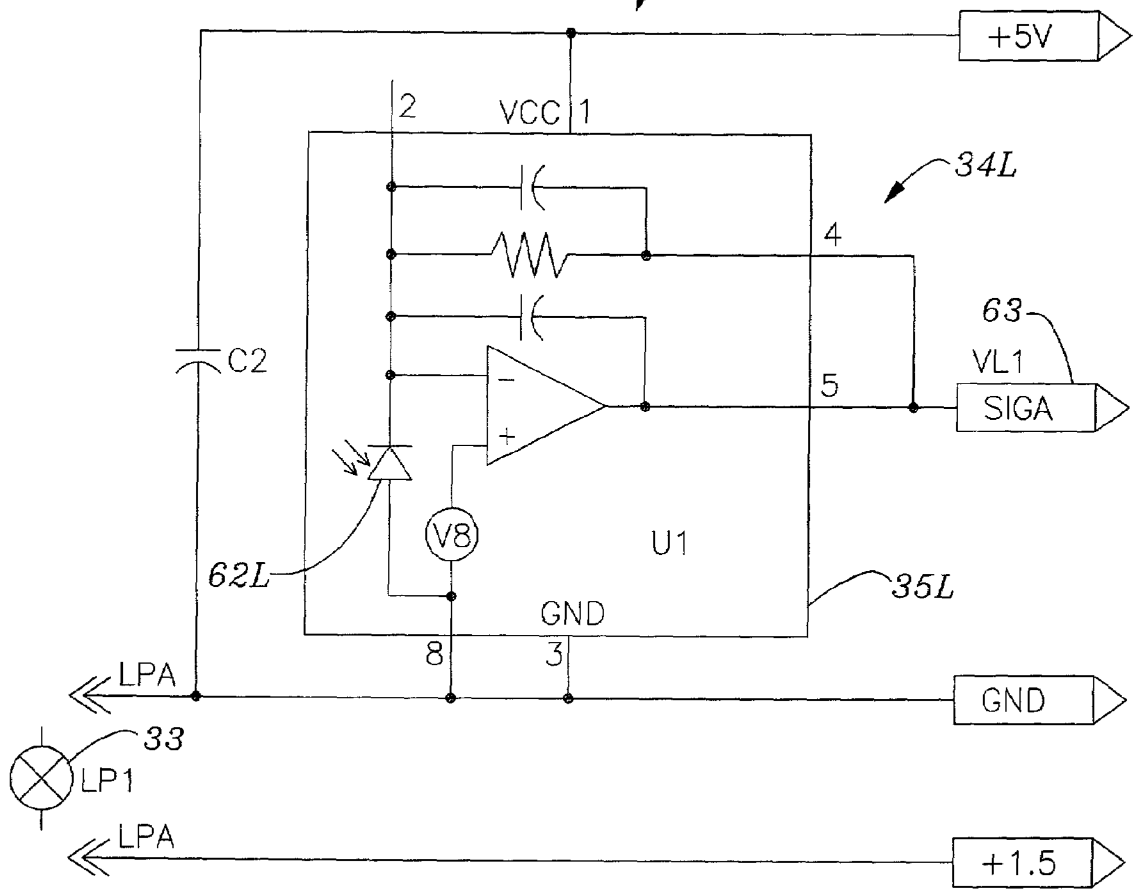
Figure 12C:
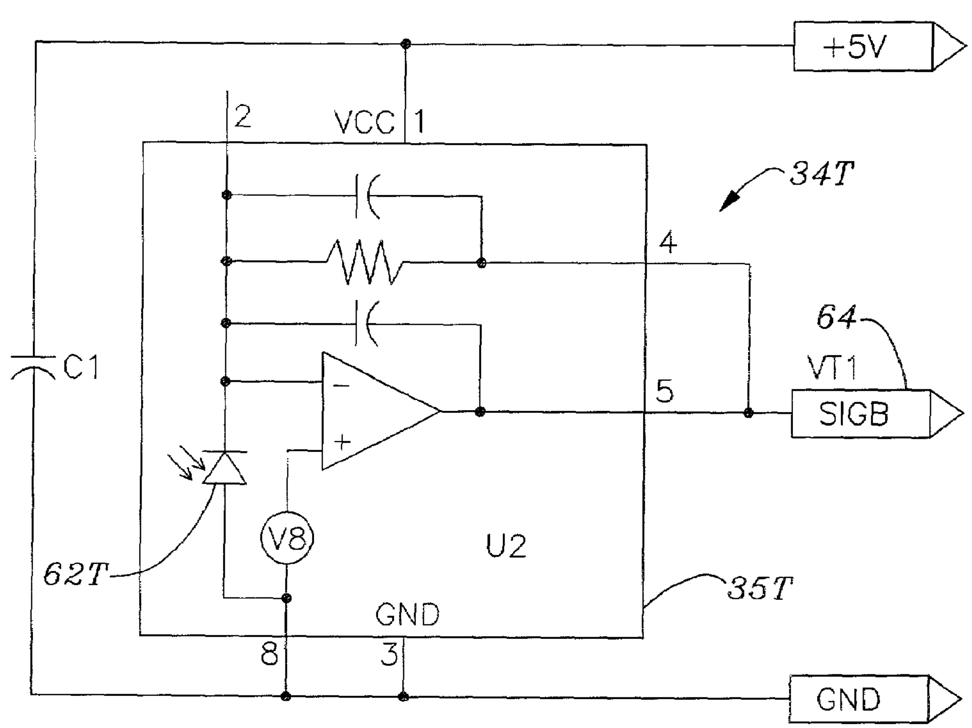
Figure 12D:
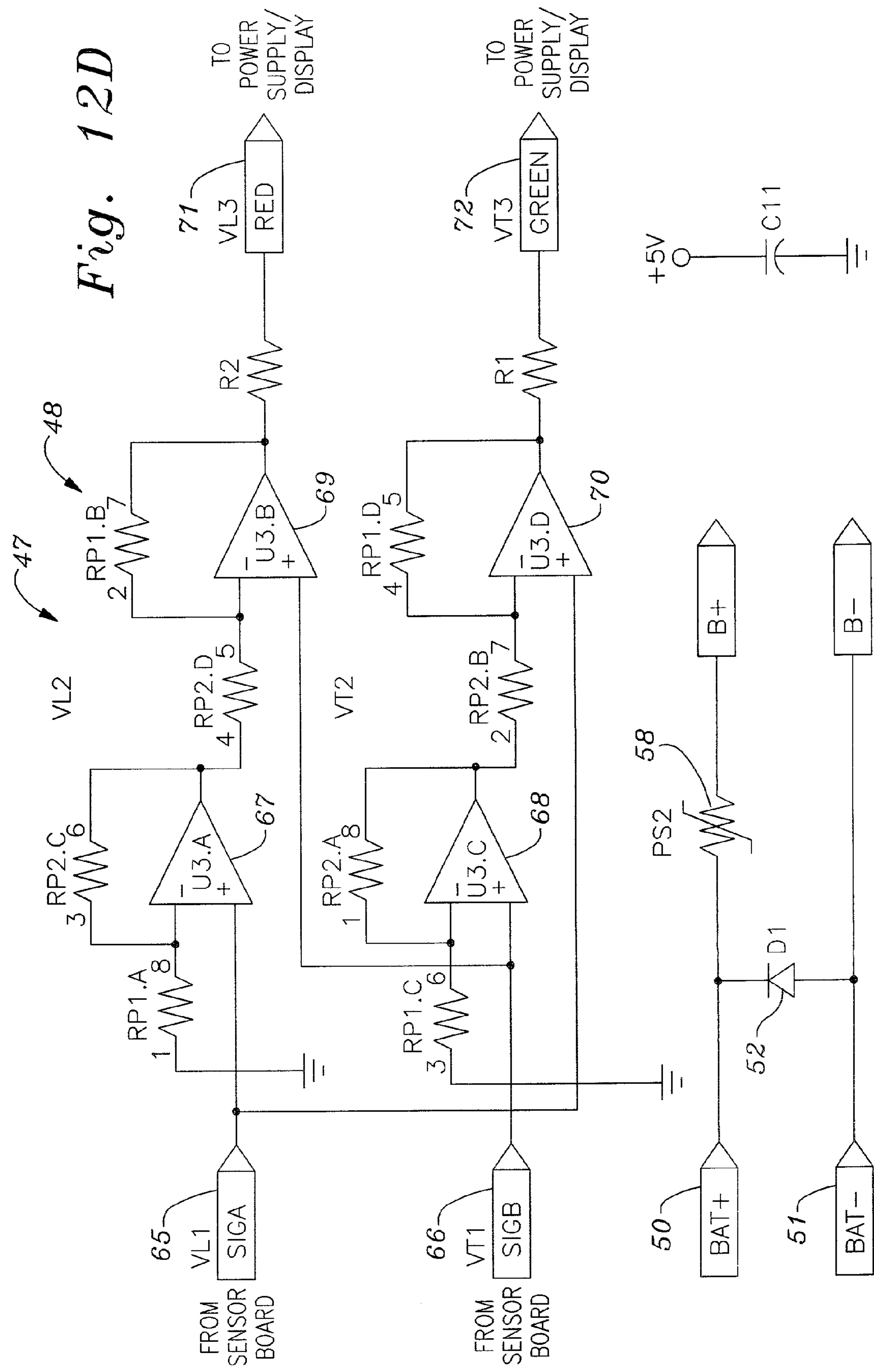
Figure 12E:
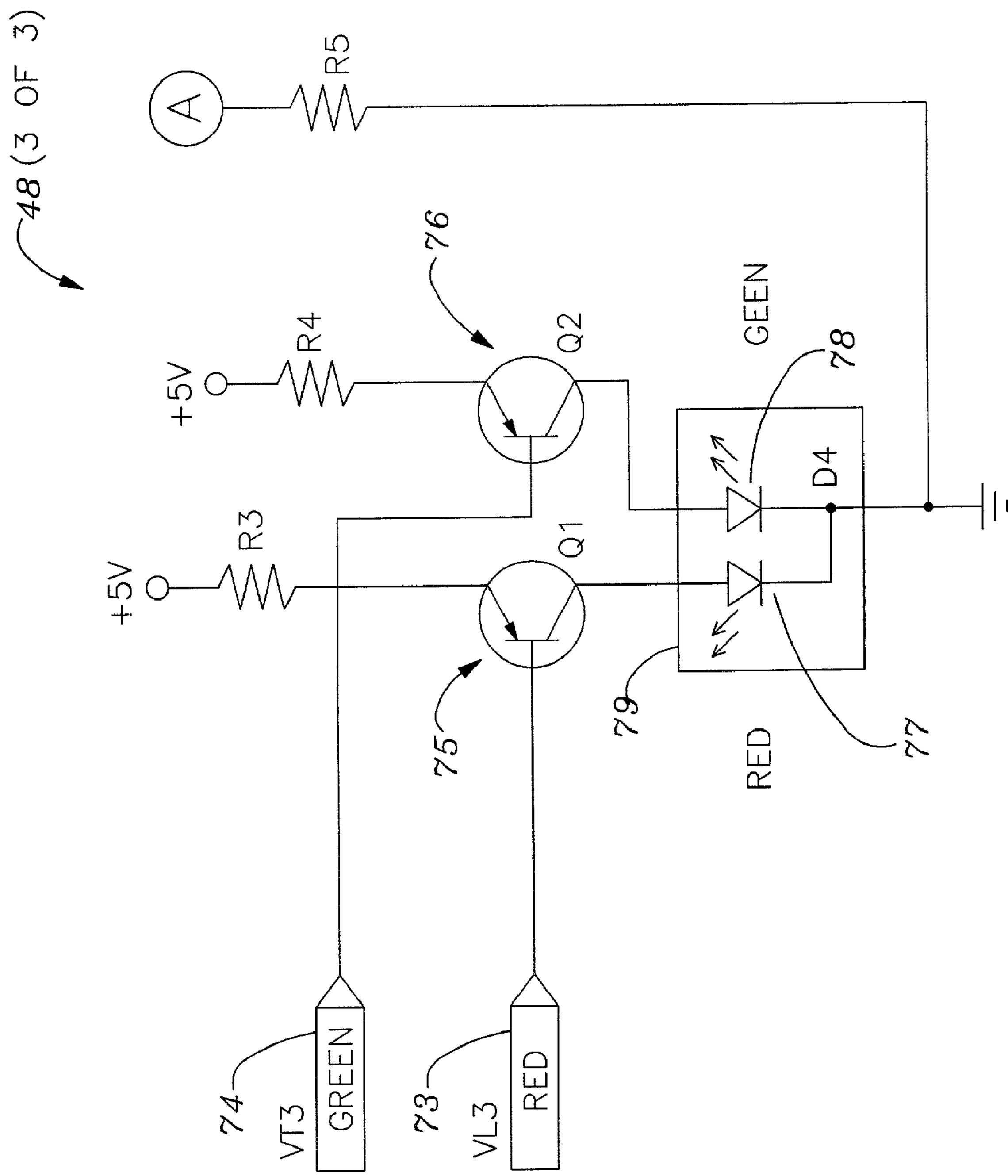

Referring to FIG. 12A, power conditioner/display module 48 contains a five-volt regulator 60 for supplying regulated five-volt current to other portions of circuitry 45, and a one-and-one-half volt regulator 61 for providing a regulated source of current for lamp 33. As shown in FIGS. 11 and 12C, optical head module 46 includes lamp 33, and photodetector assemblies 34L, 34T, the latter comprising photo diodes 62 which are mounted on integrated photodetector amplifier circuits 35L, 35T.

As shown in FIG. 12C, photodetector amplifier circuit 35L has an output terminal 63 on which occurs a voltage VL1 proportional to the intensity of light irradiating photo diode 62L of leading photodetector assembly 34L. Similarly, photodetector amplifier circuit 35T has an output terminal 64 on which occurs a voltage VT1 proportional to the intensity of light irradiating photo diode 62T of trailing photodetector assembly 34T. As shown in FIGS. 11, 12B, and 12C, signal voltages VL1 and VT1 on terminals 63 and 64 proportional to light flux incident upon photodetector assemblies 34L, 34T respectively, are input to signal input terminals 65, 66 of signal processing module 47. The latter contains leading and trailing buffering operational amplifiers 67, 68, respectively, and leading and trailing difference amplifiers 69, 70, respectively. The latter have output terminals 71, 72, respectively, which are connected to signal input terminals 73, 74 of power conditioner/display module 48.

As shown in FIG. 12A, signal input terminals 73, 74 of power conditioner/display module 48 are connected to the bases of a pair of PNP amplifier transistors 75, 76. The emitters of the transistors are connected to a regulated positive five-volt supply bus, and the collectors are connected the anodes of red and green indicator light emitting diodes (LED's) 77, 78, respectively. LED's 77, 78 are both contained in a single housing or envelope 79, and have cathodes that are connected to the ground of circuitry 45. As shown in FIG. 1, LED housing 79 is located behind a transparent circular window 80 in upper wall 26 of tester housing 21.

Signal processing module 47 cooperates with optical head module 46 and power conditioner/display module 48 to selectively illuminate red, leading LED 77 and/or green, trailing LED 78, in a manner which may be best understood by referring to FIGS. 12A, 12B, and 12C. As those familiar with the function of operational amplifiers may easily verify, the voltage output on leading, red output terminal 71 of signal processing module 47 is related to signal input VL1 from leading photodetector amplifier 35L by the equation:

$$VL3=101\ (VT1-VL1) \quad \text{(eqn 1)}$$

Similarly, the voltage output of trailing, green output terminal 72 of signal processing module 47 is related to signal input VT1 from trailing photodetector amplifier 35T by the equation:

$$VT3=101\ (VL1-VT1) \quad \text{(eqn 2)}$$

Since operational amplifiers 67, 68, 69, and 70 of signal processing module 47 are powered by a unipolar, e.g., positive five-volt power source, it is clear that the output voltages VL3, VT3 both can have values ranging between zero volts and plus five-volts.

Referring now primarily to FIG. 12A, it may be seen that current is conducted to LED 77 by drive transistor 78 when VL3 is below the difference between the five-volt supply and the cut-in voltage of the emitter-base junction of transistor 75, e.g., about 4.4 volts or lower. Thus, from equation 1, if VL1 exceeds VT1 by a threshold voltage of about 6 mV of amplifier 69, red, leading LED 77 will be illuminated. Similarly, from equation 2, if VT1 exceeds VL1 by the same threshold voltage of about 6 m V, green trailing LED 78 will be illuminated. That threshold corresponds to an irradiation of about 0.1 milliwatts/$cm^2$ on photo diode 62.

As shown in FIGS. 1 and 12A, electrical power is supplied to electronic circuitry 45 of tester 21 by depressing a push-button 82 of a momentary contact push-button switch 81. As shown in FIG. 1, switch 81 is mounted below upper wall panel 26 of tester housing 21 with push-button 82 protruding upwards through hole 83 provided through the upper wall panel. As shown in FIGS. 1 and 8, switch 81 is located near front window cap 30 of tester 20, placing the switch in a position easily operable by the thumb of a person grasping tester housing 21 in his or her hand.

Operation of blanching response tester 20 according to the present invention is illustrated in FIG. 8 and described as follows. As shown in FIG. 8, front surface 38 of lens block 37 in front window cap 30 of tester 20 is pressed down on a sample reference area of known good skin on a patient's body, near a questionable area to be tested for pressure sores. While the exact value of pressure is not critical, the pressure should be approximately equivalent to that exerted by the thumb in performing a normal blanch response test. A convenient way for an operator to determine the proper amount of pressure to be applied to a patient's skin in utilizing tester 20 is to press lens block 37 against healthy light colored skin with pressure sufficient to achieve a noticeable blanch or whitening of the skin when the tester is withdrawn from contact with the skin to release the pressure exerted thereon.

Tester 20 is used to detect first stage pressure sores by depressing push-button 82 of power on/off switch 81 while lens block 37 is pressed against the skin of the patient, with a suitable amount of pressure determined as described above. With push-button 82 depressed, tester 20 is slowly slid laterally in the direction of a vector pointing from trailing lens block window 42T towards leading lens block window 42L, i.e., in the direction of the arrows 83 printed on upper wall panel 26 of the tester, while maintaining the required pressure. In this manner, the device is slid across a questionable area and into areas of known good skin. During this test procedure, light source 33 illuminates an area of the skin adjacent to leading and trailing photodetector windows 42L 42T with broad-band illumination ranging from visible to near infrared portions of the electromagnetic spectrum. Portions of the light supplied from light source 33 penetrate the skin and are reflected from tissues and fluid below the skin. If skin below the leading photodetector window 42L is underlain by pooled-up blood or fluids symptomatic of a non-blanchable erythema, more light will be reflected back onto leading photodetector 35L than into trailing photodetector 35T. If the difference in irradiance of photodetector 35L and 35T exceeds a threshold value of about 5% to about 15%, red LED 77 will be illuminated by electronic circuitry 45, thus giving a positive indication of a non-blanchable erythema.

To determine the boundaries of a non-blanchable erythema detected and indicated by the illumination of red LED 77 as described above, push-button 82 is released, and the test procedure described above repeated numerous times, sliding lens block 37 along lines radiating from a questionable areas in various directions to determine the shape and area of the non-blanchable erythema.

Figure 9:
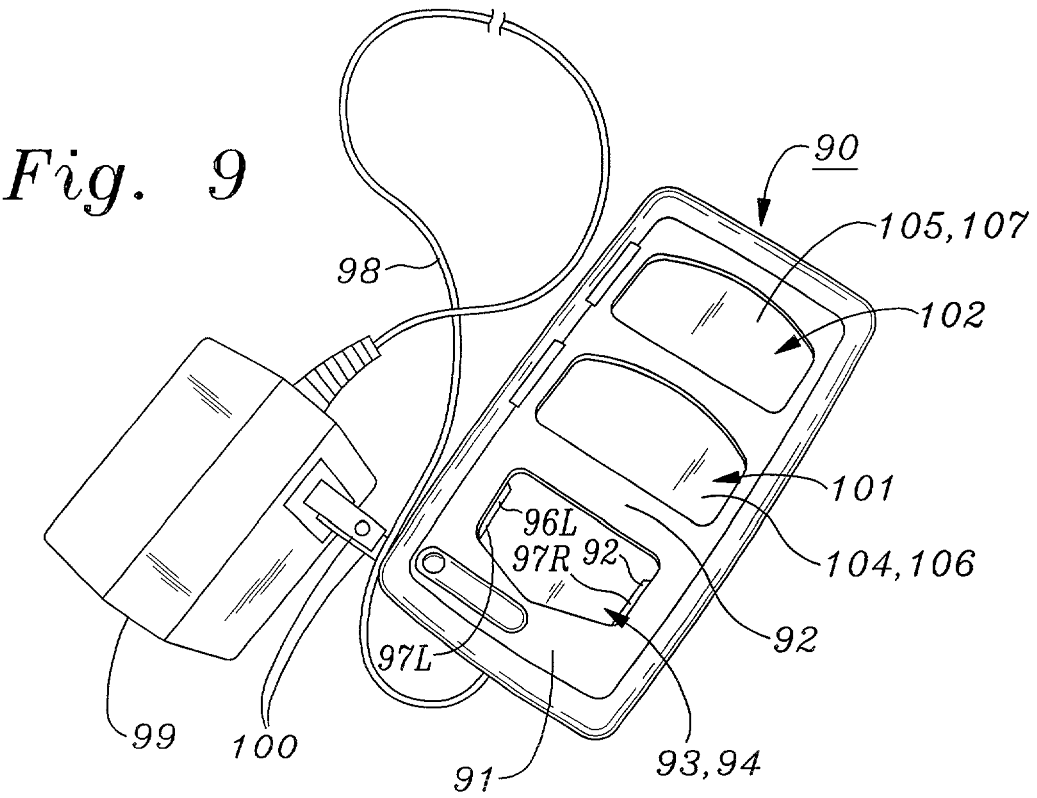
FIG. 9 is an upper perspective view of a battery charger and test/calibration module for use with the apparatus of FIG. 1.

Blanching response tester 20 according to the present invention preferably includes an auxiliary calibration test apparatus for confirming proper operation of the tester prior to its use on a patient. A preferred embodiment of such a calibration apparatus also includes a battery charger for charging rechargeable battery 49 of BRT tester 20. Thus, as shown in FIG. 9, an auxiliary calibration test/charger apparatus 90 for use with blanching response tester 20 may be seen to include a shallow rectangularly shaped box-like housing 91. Housing 91 has formed in upper wall panel 92 thereof a first, rear polygonally-shaped aperture 93 opening downwardly into a well 94 shaped to congruently and insertably receive rear end portion 95 of tester 20. Left and right side walls 96L, 96R of rear well 94 have protruding therefrom a pair of resiliently outwardly biased contacts 97L, 97R adapted to electrically contact charger terminals 50, 51 protruding outward from left and right side walls 22, 23, respectively of tester housing 21. Charger contacts 97L, 97R, are connected through a power cable 98 to a power pack 99 which encloses a transformer and rectifier. Power pack 99 has a pair of connector blades 100 adapted to be plugged into a wall receptacle connected to an alternating current power main.

Figure 13:
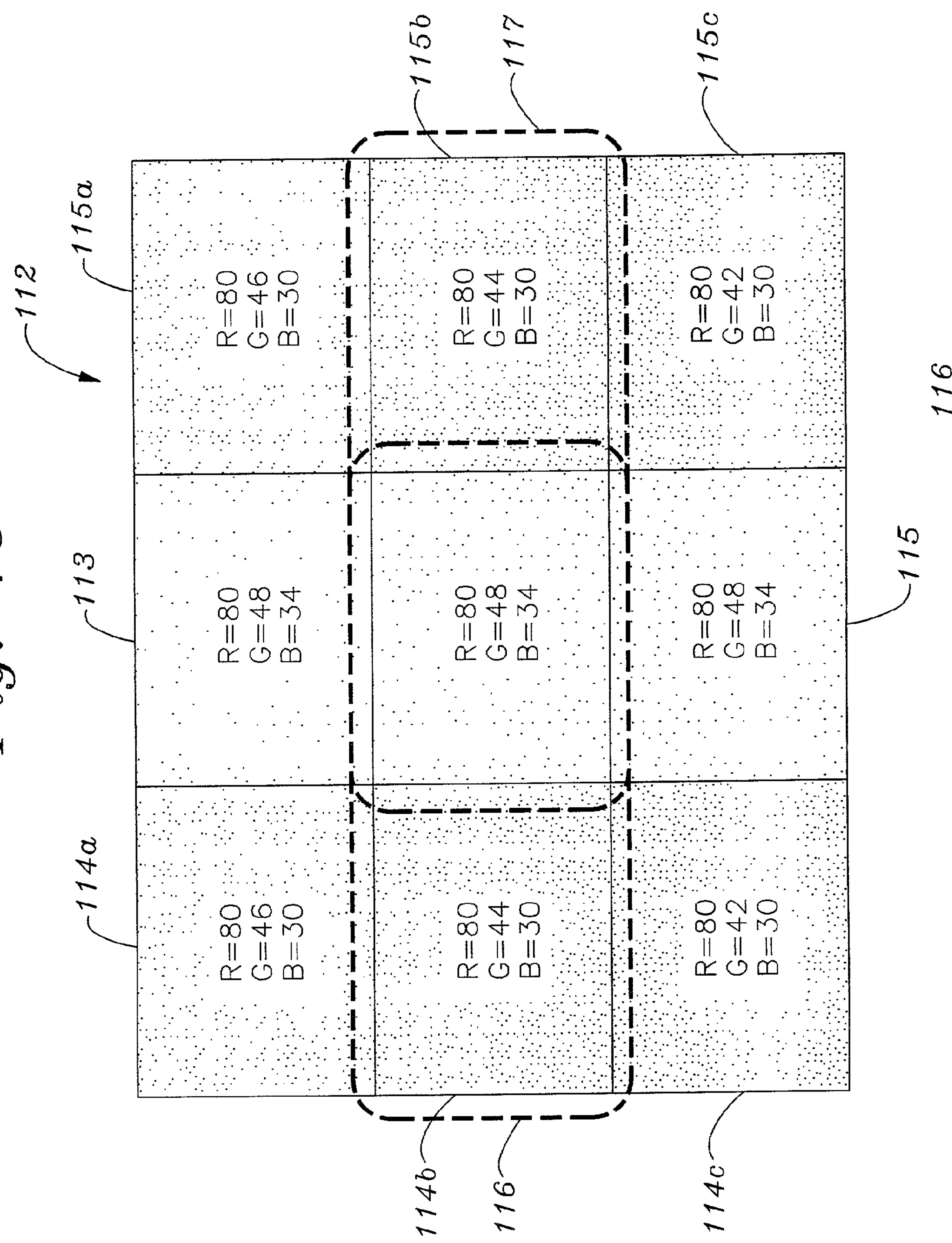
FIG. 13 is a partly diagrammatic view of a color sensibility test chart used to calibrate and make test templates for the apparatus of FIG. 1.

As shown in FIG. 9, calibration test/charger apparatus 90 also includes a middle calibration well 101 and a front calibration well 102 spaced longitudinally forward of rear charger well 94. Middle and front wells 101, 102 are of a proper size and shape to insertably and conformally receive a front end portion 103 of tester 20. Middle and front calibration wells 101, 102, have flat lower walls 104, 105 holding calibration sheets or templates 106, 107, respectively. The latter have an outline shape congruent with the shapes of the wells. As shown in FIG. 13, each template has a laterally centrally located, longitudinally disposed rectangular column strip of a first color, and a pair of symmetrically-shaped but different colored left and right, horizontally disposed rectangular bars. A front "NO-GO" template 107 for use in front well 102 has a left or leading side area 108 that has a greater spectral reflectance in the 530–590 nm range than does right, or trailing side area 109. The ratio of leading and trailing spectral reflectances of leading and trailing areas 108, 109 is chosen to typify a ratio of reflectance of skin area overlying an area having a non-blanchable erythema, to that of a healthy area of skin. Thus, when tester 20 is inserted into front NO-GO test well 102 holding NO-GO template 109, red LED 77 of tester 20 will be illuminated when push button 82 is depressed if the tester is properly calibrated and functioning, and will not light if the tester is not properly calibrated or malfunctioning.

In an exactly analogous manner, GO template 106 for middle well 101 is made with its left or leading side 110 having less spectral reflectance than right, or trailing side 111. Therefore, inserting a tester 20 into middle, GO well 101 and depressing push button 82 will cause green LED 78 to be illuminated if the tester is properly calibrated and functioning, and not illuminate it the tester is not properly calibrated or malfunctioning.

GO/NO-GO templates 106, 107 are made as follows. First, a photograph is taken of a typical dark-skinned individual whose skin color is representative of a skin color through which a pressure sore could not be detected by the standard manual thumb blanching test, because of skin pigmentation. Next, the RGB (red, green, blue) values of the image are measured, and the spectral characteristics of the image modified by adding or subtracting incremental percentages of RGB (red, green, blue) values associated with the colors of hemoglobin and deoxyhemoglobin (530 to 590 nm). Thus, colors of images may be shifted towards red, longer wavelengths by adding R values, or by subtracting G or B values, to thereby simulate spectral characteristics or signatures which identify the presence of a non-blanchable erythema.

FIG. 13 illustrates how a color sensitivity test chart 112 is used both to determine the threshold sensitivity of BRT detector apparatus 20 to detecting non-blanchable erythemas in darkly pigmented skin, and to prepare GO template 106 and NO-GO template 107. As shown in FIG. 13, chart 112 includes a central vertically elongated, rectangularly-shaped column stripe 113 printed on a sheet of white paper or card stock, with color hue and saturation values which closely approximate those in a photograph of a typical dark-skinned individual. A Canon BJ 2100 model ink jet printer and a Hewlett-Packard Color LJ5M model laser color printer both have been found to satisfactorily perform the aforementioned tasks, although any suitable color printing technique may be used. Next, a vertical series of horizontally elongated, rectangularly-shaped left and right row bars 114, 115, respectively, are printed on opposite lateral sides of central vertical stripe 113. Left and right bars 114, 115 are colored similarly to central stripe 113, but contain decreasing percentages of green relative to R and B values, corresponding to increasingly severe non-blanchable erythemas. For example, a first row of left and right bars 114*a*, 115*a* in FIG. 13 contain RGB values of 80, 46, 30, respectively, while the RGB values of central stripe 113 are 80, 48, and 34. Similarly, bars 114*b*, 115*b* in the second row of FIG. 13 have RGB values of 80, 44 and 30, and bars 114*c*, 115*c* in the third row have RGB values of 80, 42, and 30.

Chart 112 is used to calibrate tester 20 as follows: Window or lens block 37 of tester 20 is positioned against the upper surface of chart 112 with leading photodetector 35L over a horizontal bar, e.g., 114*a* and trailing photodetector 35T over central stripe 113. Red and green LEDs 77, 78 are observed. Tester 20 is then translated longitudinally to position leading photodetector 35L over a different horizontal bar, e.g., 114*b*. When red 77 is illuminated with tester 20 over a bar 114 (N) having a particular difference in RGB values from central stripe 113, and is not illuminated with the tester positioned over a bar 114 (N−1) having a smaller difference in RGB values, the threshold sensitivity of the tester is determined. Using this information, a NO/GO template 107 is prepared by cutting from test chart 112 a left laterally elongated rectangular portion 116 containing a left bar 114, e.g., 114*b* and a portion of center stripe 113, as shown in FIG. 13. Similarly, a GO template 106 is prepared by cutting from an identical test chart 112 a portion 117 containing a portion of central stripe 113 and a right bar 115, e.g., 115*b*. It should be noted that the RGB values of left and right bars used to make NO/GO and GO templates 107, 106, respectively, need not be the same. Thus, for example a GO template 106 could be prepared using row 3 of FIG. 13, i.e., using right bar 115*c*, corresponding to a greater difference in RGB values than NO/GO template 107 using second row 114*b*.

In performing the initial calibration procedure described above, it was found advantageous to make the overall sensitivity of the leading and trailing optical/electronic gain transfer function products of leading and trailing channels slightly different to enhance the detection capability of BRT tester 20. Thus, it was found advantageous to either decrease the light sensitivity of leading or trailing photodetectors by vignetting, for example, or decreasing amplifier gain. The reason that this imbalance works is that is presets or biases the device slightly into the "GREEN" to indicate to the clinician that the skin is healthy. Unhealthy condition shifts into "RED."

It is important to note that the blanching response tester according to the present invention provides GO/NO-GO indications of incipient pressure sores on a patient, by merely pressing the tester against a suspected skin area. Thus, the tester according to the present invention provides a static indication of pressure sores, and does not required that the tester be dragged or otherwise moved across the surface of the skin, which might cause discomfort or harm to a patient.

Also, red and green LED NO-GO, GO indicators 77, 78 can be supplemented or replaced by an audible sound producing transducer which emits two different audibly distinct tones signifying NO-GO and GO test results, respectively.

What is claimed is:

1. An apparatus for detecting the presence of a non-blanchable erythema symptomatic of a pressure sore in human tissue, said apparatus comprising;

a. a housing, b. an optically transmissive window located in a wall of said housing, said window having an outer surface pressable against human tissue and thereby cause said tissue to blanch, c. a light source located within said housing inwardly of said window, said light source being energizable to emit light outwards through said window to the exterior of said housing, d. a first, leading photodetector having a field of view through said window which includes a first region spaced from said light source in a first direction, e. a second, trailing photodetector having a field of view through said window which includes a second region spaced apart in a second direction from said light source, f. signal processing means having input terminals connected to said leading and trailing photodetectors and at least a first output terminal which outputs a signal indicative of which photodetector output signal is larger, said signal processing means including a first differential amplifier having a first input terminal connected to an output terminal of said leading photodetector, and a second input terminal connected to an output terminal of said trailing photodetector, and a second differential amplifier having a first input terminal connected to an output terminal of said trailing photodetector, and a second input terminal connected to an output terminal of said leading photodetector, g. indicator means connected to said signal processor means and providing a first type perceptible indicator response to a first-type output signal from said signal processing means, and a second-type perceptible indicator response to a second-type output signal from said signal processing means, said indicator means including a first annunciator which provides a first-type perceptible signal if said output signal from said leading photodetector exceeds by a first pre-determined threshold value an output signal from said trailing photodetector, and a second-type perceptible signal if said output signal from said trailing photodetector exceeds by a second pre-determined threshold value an output signal from said leading photodetector, and h. a first, NO-GO test/calibration template, said first template having thereon a first, leading colored test pattern positionable against said window underneath said leading photodetector, and a second, trailing colored test pattern simultaneously positionable underneath said trailing photodetector, said first colored test pattern having hue and saturation levels corresponding to that of a non-blanchable, erythema, and said second colored test pattern having hue and saturation levels corresponding to that of healthy tissue, said first and second test patterns being sufficiently different in hue and saturation levels to cause said first annunciator to output said first-type perceptible signal.

2. The apparatus of claim 1 wherein said first annunciator means is further defined as being a first light emitting diode connected to an output terminal of said first differential amplifier.

3. The apparatus of claim 2 wherein said indicator means is further defined as including a second light emitting diode connected to an output terminal of said second differential amplifier.

4. The apparatus of claim 3 wherein said second light emitting diode emits light of a different wavelength than that emitted by said first light emitting diode.

5. The apparatus of claim 3 wherein said first and second light emitting diodes are both located behind a single lens viewable from the exterior of said housing.

6. The apparatus of claim 1 further including a second, GO test/calibration template, said second template having thereon a third trailing colored test pattern positionable against said window underneath said trailing photodetector, and a fourth, leading colored test pattern simultaneously positionable underneath said leading photodetector, said third colored test pattern having hue and saturation levels corresponding to that of a non-blanchable erythema, and said fourth test pattern having hue and saturation levels corresponding to that of healthy tissue, said third and fourth test patterns being sufficiently different in hue and saturation levels to cause said annunciator to output said second-type perceptible signal.

7. A method for detecting the presence of a non-blanchable erythema symptomatic of a pressure sore in human tissue, said method comprising;

a. positioning an optically transmissive body adjacent to a first, NO-GO test/calibration template, said first template having thereon a first, leading color test pattern positionable against said optically transmissive body underneath a first, leading photodetector, and a second, trailing colored test pattern simultaneously positionable underneath a second, trailing photodetector, said first colored test pattern having hue and saturation levels corresponding to that of a non-blanchable erythema, and said second colored test pattern having hue and saturation levels corresponding to that of healthy tissue, said first and second test patterns being sufficiently different in hue and saturation levels to cause a difference in electrical signal output levels from said photo detectors to thereby establish a first threshold value, b. pressing said optically transmissive body against an area of human tissue, c. illuminating said area of tissue by means of light emitted from a light source and passing through said optically transmissive body, d. receiving a first light sample emitted by said light source and reflected from a first, test region of said tissue area by first photodetector means providing a first photodetector output signal proportional to the intensity of said first light sample, e. receiving a second light sample emitted by said light source and reflected from a second, standard region of said tissue area by second photodetector means providing a second photodetector output signal proportional to the intensity of said second light sample, f. comparing the magnitudes of said first and second photodetector output signals and providing a first type of indicator signal if said first photodetector output signal exceeds said second photodetector output signal by said first pre-determined threshold value, and g. providing a second-type indicator signal if said second photodetector output signal exceeds said first photodetector output signal by a second pre-determined threshold value.

8. The method of claim 7 further including the step of positioning an optically transmissive body adjacent to a second, GO test/calibration template, said second template having thereon a third, trailing color test pattern positionable against said optically transmissive body underneath said trailing photodetector, and a fourth, leading colored test pattern simultaneously positionable underneath said leading photodetector, said third colored test pattern having hue and saturation levels corresponding to that of a non-blanchable erythema, and said fourth colored test pattern having hue and saturation levels corresponding to that of healthy tissue, said third and fourth test patterns being sufficiently different in hue and saturation levels to cause a difference in electrical output levels from said photodetectors to thereby establish said second threshold value.

9. The method of claim 7 further including the step of comparing the magnitude of said second and first photodetector output signals and providing a second type of indicator signal if said second photodetector output signal exceeds said first photodetector output signal by a second pre-determined threshold value.

10. The method of claim 7 wherein at least a portion of energy emitted by said light source is in the approximate wavelength range of 0.8μ to 1.5μ.

11. The apparatus of claim 10 wherein said light source is further defined as including an incandescent lamp.

* * * * *